United States Patent [19]

Gross

[11] 4,001,939
[45] Jan. 11, 1977

[54] TOOTH-FILLING MATERIAL BASED ON SYNTHETIC PLASTICS MATERIAL

[75] Inventor: Albert Gross, Frankfurt, Germany

[73] Assignee: Kulzer & Co. GmbH, Bad Homburg, Germany

[22] Filed: Nov. 20, 1972

[21] Appl. No.: 308,084

Related U.S. Application Data

[63] Continuation of Ser. No. 140,279, May 4, 1971, abandoned, which is a continuation of Ser. No. 751,357, Aug. 9, 1968, abandoned.

[30] Foreign Application Priority Data

Aug. 19, 1967 Germany .......................... K 63146

[52] U.S. Cl. .................. 32/15; 260/42.52; 260/875; 260/885; 260/998.11
[51] Int. Cl.² .......................................... A61K 5/06
[58] Field of Search ........................ 106/35; 32/15; 260/41 R, 875, 885, 42.52, 998.11

[56] References Cited

UNITED STATES PATENTS

| 3,462,839 | 8/1969 | Boyer et al. ........................ 106/35 |
| 3,435,012 | 3/1969 | Nordlander .................... 260/88.3 R |
| 3,476,723 | 3/1970 | Stahl et al. ....................... 260/885 |
| 3,518,762 | 7/1970 | Takeuchi ............................ 106/35 |
| 3,539,526 | 11/1970 | Bowen ............................... 106/35 |
| 3,635,889 | 1/1972 | Bowen ............................... 106/35 |

OTHER PUBLICATIONS

Chemical Abstracts, vol. 65:15618c.
Chemical Abstracts, vol. 57:12717c.

*Primary Examiner*—James H. Derrington
*Attorney, Agent, or Firm*—Burgess, Dinklage & Sprung

[57] ABSTRACT

Tooth filling and dental fixing using a monomeric polymerizable liquid and a polymer in powder form, which can be a mixture of monomeric and polymeric methyl methacrylates. Adhesion is increased by using a hydroperoxide of the formula ROOH in which R is an optionally substituted alkyl radical.

38 Claims, No Drawings

TOOTH-FILLING MATERIAL BASED ON SYNTHETIC PLASTICS MATERIAL

This application is a continuation of application Ser. No. 140,279, filed May 4, 1971, now abandoned which is a continuation of application Ser. No. 751,357, filed Aug. 9, 1968, now abandoned.

This invention relates to a tooth-filling material based on synthetic plastics material, in particular a filling material consisting of monomeric polymerisable liquid and polymer in powder form.

It has already long been known to use plastic mixtures of polymerisable liquid monomers and polymers in powder form, more expecially mixtures of monomeric and polymeric methyl methacrylates or corresponding multi-component mixtures for filling tooth cavities and also for fixing inlays of synthetic plastics or metal. In this connection, generally a mixture, which can be semi-fluid to pasty, and which consists of the monomeric liquid and the pulverous polymer, is formed into a paste and is allowed to harden in the mouth of the patient, advantageously under the influence of polymerisation catalysts and/or accelerators, which cause the polymerisation of the monomer and thus the hardening or curing of the mixture of synthetic plastics.

These plastic fillings have per se proved to be very satisfactory as compared with the otherwise usual amalgam and silicate fillings, since on the one hand they do not give any rise to element formation, such as is unavoidable with amalgam filling when a metallic tooth replacement or other metals is simultaneously present, and on he other hand they are more satisfactory cosmetically and are not so easily washed out, as is frequently the case with silicate fillings. However, because of their entirely different chemical structure as compared with the tooth substance, namely, both as compared with the dentine and also the tooth enamel, the plastic fillings tend to be ground down and worn away more quickly by the various influences in the mouth and not least of all by the mechanical influences when chewing, so that they have to be frequently renewed. In order substantially to adapt the properties of the plastic fillings to that of the tooth substance, tests have been repeatedly carried out in order to improve the mechanical properties of the plastic fillings usually by use of inorganic fillers. Thus, it is already known to use in combination fine glass and quartz beads, sometimes in a very high proportion, in the mixture, these being almost completely enclosed by the synthetic plastic material during the curing of the plastic mixture and considerably increasing its mechanical properties, without particles of the filler becoming detached on chewing and thus having a deleterious effect on the filling, which frequently cannot be avoided with sharp-edged fillers.

Both the plastic fillings with fillers and those without fillers do however frequently show disadvantages as regards the bonding strength on the dentine and also on the tooth enamel, and this is mainly to be appreciated from the fact that when the filling is placed in position and cured, fine gaps are formed at many places between the tooth cavity and filling which initially are not recognisable but into which in time residues of food and decomposition products are able to diffuse, and these cause discoloration and even lead to secondary caries being initiated, the filling becoming loose and completely or partially falling out so that it has to be renewed; frequently the result is even destruction of the pulp and loss of the tooth. These undesirable accompanying phenomena of most of the filling materials and also of the plastic fillings are, however, also to be observed when inlays of metallic dental materials, such as gold and other precious metals or precious metal alloys, are fixed by means of synthetic plastics materials in the cavity and when other metallic parts of protheses, for example, parts of bridges, are anchored in the mouth by means of plastics.

It has now surprisingly been found that the adhesion of plastic mixtures consisting of monomeric liquid and pulverulent polymers, and indeed also with a high content of filling material, to the dentine and tooth enamel and also to the metallic prothesis materials can be quite considerably improved and the formation of any gaps between the natural and the unnatural material can practically be completely avoided if the tooth-filling or dental fixing material contains at least one hydroperoxide of the general formula ROOH, in which R is an optionally substituted alkyl radical, in which the bond with the -OOH-group is achieved by way of a primary, secondary or tertiary carbon atom. Instead of the said hydroperoxides, it is also possible to use those compounds from which the hydroperoxides are formed in situ. The invention therefore provides a tooth-filling material and dental fixing material based on synthetic plastics, comprising a monomeric polymerisable liquid and polymer in powder form, and containing at least one hydroperoxide of the general formula ROOH, or a compound from which such a hydroperoxide is forced in situ, in which R is an optionally substituted alkyl radical, the bonding with the -OOH-group being effected by way of a primary, secondary or tertiary carbon atom.

It is particularly advantageous for the plastic mixture to contain 0.1 to 5% by weight, advantageously 0.3 to 3% by weight and particularly 0.5 to 1 by weight of an alkyl hydroperoxide, based on the monomeric liquid.

As alkyl hydroperoxide, there are especially to be considered those of which the alkyl radical contains up to 12 carbon atoms, advantageously those with 3 to 6 carbon atoms in the alkyl radical. The alkyl peroxides which have proved especially suitable for the purposes of the invention are the n-propyl, n-butyl, n-amyl and n-hexyl hydroperoxides, as well as butyl-dimethyl carbinol hyperoxide and in particular tert.-butyl hydroperoxide. An example of a compound from which a hydroperoxide is formed in situ, i.e. when using the material, is tri-tert.-butyl peroxyboron but other hydrolysable per esters can also be used.

The hydroperoxides or the compounds from which the hydrperoxides are formed in situ are preferably added to the monomeric component of the plastic mixture to be polymerised, but the addition can also be made when the monomeric liquid and the pulverulent polymer are already formed into a paste. However, it is obviously also possible to add the alkyl peroxide to a suitable priming substance, e.g. to the solution of a suitable film former in a solvent with which the dentine surface of the tooth cavity is brushed out before inserting the plastic filling. In all cases, a decided improvement in the adhesion of the plastic filling to the dentine and to the tooth enamel is to be found.

However, it is also particularly surprising that this improvement in the adhesion or bonding of the plastic filling materials is not only obtained between natural tooth materials and synthetic plastics materials, but also between plastic materials and metallic dental material, for example, when fixing a gold inlay in a suitably prepared tooth cavity.

It is still not entirely clear to what the better bonding strength between tooth substance and plastic filling or between plastic and metal when using the alkyl hydroperoxides in the plastic mixtures according to the invention is to be attributed, but it is assumed that with the adhesion of the plastic to the dentine, the bond is established through the organic constituents of the tooth, possibly in the form of a graft polymerisation.

The efficacy of the alkyl hydroperoxides as regards improving the adhesion strength of tooth filling or dental fixing material consisting of a mixture of monomeric liquid and polymer in powder form is largely independent of the nature of the monomer and of the polymer, for both the monomer and polymer mixtures and also mixed polymers which are known for dental purposes can be used as constituents of the tooth-filling material. Furthermore, no limitation is necessary in respect of inorganic fillers, as it is known that in fact glass and quartz beads with an extremely small bead diameter have indeed proved particularly suitable as fillers for dental materials. This also applies as regards corresponding sections of fibres. The inorganic constituents can with advantage be pretreated with adhesion promoters, e.g. silanes, in known manner.

The plastic mixtures which harden at low temperature contain polymeisation catalysts and accelerators which are known per se, so that the curing also takes place in a short time at these low temperatures, for example, within 7 to 8 minutes at body temperature, such catalysts and accelerators usually being Redox systems, for example, combinations of peroxides and tertiary amines or of peroxides and slphur compounds, as for example sulphinc acids. The alkyl hydroperoxides generally do not have any negative influence on the efficiency of these catalyst systems, i.e. the monomer-polymer mixtures are cured without any difficulties, even with addition of the alkyl hydroperoxides as an agent for improving adhesion. However, if contary to expectation, a retarding of te curing should occur with complicated catalyst systems, particularly when the quantities of hydroperoxide are used in the upper limits of the quantities indicated, this disadvantage can easily be overcome by adding a small amount of a regulator as known per se, such as dodecyl mercaptan.

It has been proved to be particularly advantageous especially with the use as a tooth-filling material, for the mixtures according to the invention to have added thereto a small quantity of up to about 5%, based on the monomeric liquid, advantageously less then 3% and more especially up to 1%, of boric acid. Instead of boric acid, it is also possible to use those boron compounds which supply boric acid under the conditions in which the plastic mixture is used, as for example, borates of the type of tributyl borate or trioctyl borate. When using these compounds, it is in fact surprising that the tooth pulp, when introducing the plastic filling, is protected against the toxic influences of the monomer and catalyst constituents of the plastic mixture, so that necrosis and death of the pulp, which are to be attributed to the synthetic plastic and its constituents, can be almost completely excluded whenthe tooth cavity is expertly filled.

The adhesion-improving properties of the plastic mixtures according to the invention, i.e. the bonding strength values, have also been determined and checked on a material comparable with dentine, namely ivory, as well as on dentine. Moreover, tests were carried out in order to establish the bonding strength of the hydroperoxide-containing plastic mixtures on tooth enamel, on horn and also on metallic dental materials, namely, on 18-carat gold, as well as stainless steel.

For the stripping tests, there was used a stripping apparatus which also used in similar manner by the American Bureau of Standards and which is described by way of example in studies on Dental Self-curing Resins (4) Rep. Res. Inst. Dent. Mat. Tokio Med. & Dent. Univ. Vol. 2, No 6 (1964) page 521 et seq. The adhesion position investigated was on a test element which was embedded in a specimen holder and was protected against bending loads, said position being circular and having a diameter of 5 mm, i.e. an area of about 0.2 cm$^2$.

As well as stripping tests, measurements of the shearing strength were also carried out, for which purpose there was used the arrangement described by Uy and Chang in "Adhesive restorative Dental Materials II 1965" (Public Health service publication No. 1494 (1966) Washington US Dept. of Health), page 104 et seq. With these measurements of the shearing strengths, the adhesion surface was also about 0.2 cm$^2$.

In order to make possible accurate reading of the tensile force, the specimen holders in both cases were fitted into an adapter for the measurement with the Zwick bending test machine. The forces necessary for breaking the adhesive connection can be determined between 0 and 300 kg and with an accuracy of $\times$ 0.5 kg.

As test elements for the bonding strength on the dentine, there were also used rod-shaped pieces of ivory with a diameter of 1 cm$^2$, which were kept moist by constant storage in distilled water and were only removed from the water for the adhesion and measurement operations. As compared with human tooth sections, ivory has the advantage of better reproducibility. Comparison tests on sections of extracted human teeth gave comparable measurement values. The adhesive bonds for which the plastic mixtures hereinafter explained in detail were used, were always stored for 24 hours in a water bath at 37° C in order to provide conditions similar to those existing in the mouth, before the tests for determining the bonding strength. The individual results are indicated in the following reports on the tests and the tables.

TEST 1

In order to establish the stripping resistance on ivory and tooth enamel, the test elements were embedded in a specimen holder with gypsm, and a mixture of 1 gram of pulverulent mothyl methacrylate mixed polymer and 0.5 ml of monomeric methyl methacrylate, containing a tertiary amine and benzoyl peroxide as catalysts and the alkyl hydrperoxides mentioned in the following Table 1 was introduced into and allowed to harden in a second conical portion of the specimen holder. After being stored for 24 hours in water at 37° C, the stripping tests were carried out in the apparatus referred to above, all the tests being on ivory, except one, which was on tooth enamel; the results are also set out in Table I. The abbreviation HPO has been used for the sake of simplicity for hydroperoxide.

The table also contains a comparison test without addition of an alkyl hydroperoxide, and also two tests in which were used plastic mixtures which additionally contained 1% of a borate.

Table 1

| Additives % | No. of Bonds tested | Average loading kg | Stripping resistance kx/cm² |
|---|---|---|---|
| none | all bonds immediatly broken | | |
| 0.4 tert-butyl-HPO | 4 | 2.2 | 11.0 |
| 0.7 tert.-butyl-HPO (emamel) | 3 | 41.5 | 208.0 |
| 0.7 tert.-butyl-HPO | 4 | 25.8 | 129.0 |
| 0.7 n-propyl-HPO | 4 | 11.5 | 57.5 |
| 0.7 n-butyl-HPO | 4 | 19.2 | 96.0 |
| 1.0 n-amyl-HPO | 4 | 17.5 | 87.5 |
| 1.0 n-hexyl-HPO | 12 | 15.6 | 78.0 |
| 1.0 butyldimethyl-carbinol-HPO | 4 | 21.6 | 108.0 |
| 0.7 tert.-butyl-HPO + 1.0 tributylborate | 4 | 17.9 | 89.5 |
| 0.7 tert.-butyl-HPO + 1.0 trioctylborate | 4 | 24.3 | 122.2 |

TEST 2

Using plastic mixtures according to Test 1, which contain the hydroperoxides mentioned in Table II, shearing tests were also carried out with the apparatus mentioned above and the following results were obtained. In these shearing tests, there was also investigated a mixture which contained a boron compound. Shearing tests on tooth enamel and on horn are also included.

Table II

| Additives % | bond with | No. of bonds tested | Average loading kg | Shearing strength kg/cm² |
|---|---|---|---|---|
| none | ivory | bonds immediatly broken | | |
| 1.0 n-butyl-HPO | ivory | 4 | 33.0 | 165.0 |
| 1.0 n-amyl-HPO | ivory | 4 | 21.0 | 105.0 |
| 1.0 n-hexyl-HPO | ivory | 2 | 17.0 | 85.0 |
| 1.0 butyldimethyl-carbinol-HPO | ivory | 2 | 11.7 | 58.5 |
| 0.7 tert.-butyl-HPO + 0.1 B(OH)₃ | ivory | 15 | 28.9 | 144.5 |
| 0.7 tert.-butyl-HPO | Human Enamel | 13 | 19.5 | 98.0 |
| 0.7 tert.-butyl-HPO | horn | 2 | 23.0 | 115.0 |
| 0.7 tert.-butyl-HPO + 0.1 B(OH)₃ | human dentine | 2 | 47.5 | 237.5 |

Test 3

In this test, the stripping resistance on tooth enamel and on dentine was determined when using a lacquer which was applied between the test element and a plastic mixture of the composition described in Test 1 and containing no hydroperoxide. The lacquer consisted of a solution of 10% of a film-forming methyl methacrylate copolymer in acetone, to which in one case was added 0.1% of tertiary butyl hydroperoxide.

In addition, this table contains two tests carried out on ivory, in which the ivory initially had applied thereto a priming of monomeric α-cyanacrylate, which in one case contained a hydroperoxide, and thereafter the plastic mixture free from hydroperoxide was polymerised thereon.

Table III

| Additives % | bond with | No. of bonds tested | Average loading kg | stripping resistance kg/cm² |
|---|---|---|---|---|
| lacquer without HPO | human dentine | 2 | bonds immediatly broken | |
| lacquer + 0.1 tert-butyl-HPO | human dentine | 4 | 24.8 | 124.0 |
| lacquer + 0.1 tert-butyl-HPO | human enamel | 4 | 24.9 | 124.5 |
| priming without HPO | ivory | 2 | 5.0 | 25.0 |
| priming + 0.7 tert-butyl-HPO | ivory | 4 | 14.0 | 70.0 |

Test 4

Using the plastic mixture already referred to several times, tests were carried out to determine the shearing strength on metallic test elements; here also the bonds were stored for 24 hours in water at 37° C before the tests. The quantity of added hydroperoxide, the metal being tested and the results are set out in the following Table IV, together with the results of the comparison tests in which no hydroperoxide was contained in the plastic mixture.

Table IV

| Additives % | bond with | No. of bonds tested | Average loading kg | Shearing strength kg/cm² |
|---|---|---|---|---|
| none | 18-carat gold | 1 | 6.5 | 32.0 |
| 0.7 tert.-butyl HPO | 18-carat gold | 3 | 18.0 | 90.0 |
| none | stainless steel | 4 | 3.0 | 15.0 |
| 0.7 tert.-butyl HPO | stainless steel | 9 | 13.5 | 60.8 |

As is clearly apparent from the above test results, the plastic mixtures according to the invention and containing alkyl hydroperoxide show a substantially improved bonding strength with dentine and ivory, and also enamel and metallic dental materials, and are consequently not only particularly suitable as a toth-filling material but are also useful as dental fixing material.

I claim:

1. In a tooth-filling and dental fixing material based on a polymerisable acrylate liquid, an acrylate polymer in powder form, a polymerisation catalyst and an accelerator on the basis of a redox system, the improvement which comprises as a component for said material for increasing adhesion thereof, at least one hydroperoxide of the general formula ROOH or a compound from which such a hydroperoxide is formed in situ, in which R is an optionally substituted alkyl radical, the bonding with the OOH-group being effected by way of a primary, secondary or tertiary carbon atom.

2. A material as claimed in claim 1 containing 0.1 to 5% by weight based on the monomeric liquid, of an alkyl hydroperoxide.

3. A material as claimed in claim 2 in which the amount of alkyl hydroperoxide is from 0.3 to 3% by weight.

4. A material as claimed in claim 2 in which the amount of alkyl hydroperoxide is from 0.5 to 1.0%.

5. A material as claimed in claim 1 in which the alkyl hydroperoxide contains up to 12 carbon atoms in the alkyl radical.

6. A material as claimed in claim 5 which contains an alkyl hydroperoxide with 3 to 6 carbon atoms in the alkyl radical.

7. A material as claimed in claim 1, said hydroperoxide being tertiary butyl hydroperoxide.

8. A material as claimed in claim 1, said hydroperoxide being n-butyl hydroperoxide.

9. A material as claimed in claim 1, containing glass and/as quartz or filler.

10. A material as claimed in claim 1 containing boric acid or a boron compound which supplies boric acid under the conditions of use.

11. A material as claimed in claim 10 said boron compound being a borate.

12. A material as claimed in claim 1, said acrylate polymer including methyl methacrylate polymer.

13. A material as claimed in claim 12, said acrylate liquid including methyl methacrylate.

14. A material as claimed in claim 1, the redox system comprising peroxide and tertiary amine or sulfur compound.

15. In tooth filling and dental fixing, including the step of employing a tooth-filling and dental fixing material based on a polymeisable acrylate liquid, an acrylate polymer in powder form, a polymerisation catalyst and an accelerator on the basis of a redox system, the improvement which comprises including in said material for increasing adhesion thereof, at least one hydroperoxide of the general formula ROOH or a compound from which such a hydroperoxide is formed in situ, in which R is an optionally substituted alkyl radical, the bonding with the OOH-group being affected by way of a primary, secondary or tertiary carbon atom.

16. A process as claimed in claim 15, said acrylate polymer including methyl methacrylate polymer.

17. A process as claimed in claim 15, said acrylate liquid including methyl methacrylate.

18. A material as claimed in claim 1, the hydroperoxide being at least one of n-propyl, n-butyl, n-amyl, n-hexyl, tert.-butyl and butyl-dimethyl carbinol hydroperoxide.

19. A process as claimed in claim 15, the hydroperoxide being at least one of n-propyl, n-butyl, n-amyl, n-hexyl, tert.-butyl and butyl-dimethyl carbinol hydroperoxide.

20. A material according to claim 13, the redox system being a peroxide and a tertiary amine or a peroxide and a sulfur compound.

21. A material according to claim 18, the redox system being a peroxide and a tertiary amine or a peroxide and a sulfur compound.

22. Process according to claim 15, said material containing 0.1 to 5% by weight based on the monomeric liquid of an alkyl hydroperoxide.

23. Process according to claim 22, in which the amount of alkyl hydroperoxide is from 0.3 to 3% by weight.

24. Process according to claim 22, in which the amount of alkyl hydroperoxide is from 0.5 to 1.0%.

25. Process according to claim 15, in which the alkyl hydroperoxide contains up to 12 carbon atoms in the alkyl radical.

26. Process according to claim 25, in which the alkyl hydroperoxide contains 3 to 6 carbon atoms in the alkyl radical.

27. Process according to claim 15, said hydroperoxide being tertiary butyl hydroperoxide.

28. A process according to claim 15, said hydroperoxide being n-butyl hydroperoxide.

29. Process according to claim 15, said material containing glass and/or quartz as filler.

30. Process according to claim 15, said material containing boric acid or a boron compound which supplies boric acid under the conditions of use.

31. Process according to claim 30, said boron compound being a borate.

32. Process according to claim 15, the redox system comprising peroxide and tertiary amine or sulfur compound.

33. A process as claimed in claim 15, the redox system being a tertiary amine and benzoyl peroxide.

34. A material according to claim 1, the redox system being a tertiary amine and benzoyl peroxide.

35. A material as claimed in claim 1, said polymerizable acrylate liquid being methyl methacrylate, and said acrylate polymer being mthyl methacrylate polymer.

36. A material as claimed in claim 35, wherein the hydroperoxide is at least one of n-propyl, n-butyl, b-amyl, n-hexyl, tert.-butyl and butyl-dimethyl carbinol hydroperoxide.

37. A process according to claim 15, said polymerizable acrylate liquid being methyl methacrylate, and said acrylate polymer being methyl methacrylate polymer.

38. A process according to claim 37, wherein the hydroperoxide is at least one of n-propyl, n-butyl, n-amyl, n-hexyl, tert.-butyl and butyl-dimethyl carbinol hydroperoxide.

* * * * *

UNITED STATES PATENT AND TRADEMARK OFFICE
CERTIFICATE OF CORRECTION

PATENT NO. : 4,001,939
DATED : January 11, 1977
INVENTOR(S) : Albert Gross

It is certified that error appears in the above—identified patent and that said Letters Patent are hereby corrected as shown below:

Column 3, line 36, change "sulphinc" to --sulphinic--.

Column 5, line 7, (third line of heading of last column), change "kx" to --kg--.

Column 8, line 41, change "b-amyl" to --n-amyl--.

Signed and Sealed this

Twenty-fourth Day of May 1977

[SEAL]

Attest:

RUTH C. MASON
Attesting Officer

C. MARSHALL DANN
Commissioner of Patents and Trademarks